United States Patent
Luan et al.

(10) Patent No.: US 10,344,324 B2
(45) Date of Patent: Jul. 9, 2019

(54) ELECTRICAL TRAPPING AND STRETCHING OF CHARGED BIOMOLECULES BY SINGLE ELECTRODE GATING STRUCTURE

(71) Applicant: International Business Machines Corporation, Armonk, NY (US)

(72) Inventors: Binquan Luan, Chappaqua, NY (US); Sung-wook Nam, Croton-on-Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 764 days.

(21) Appl. No.: 14/225,677

(22) Filed: Mar. 26, 2014

(65) Prior Publication Data

US 2015/0275288 A1 Oct. 1, 2015

(51) Int. Cl.
*C12Q 1/6869* (2018.01)
*G01N 27/447* (2006.01)
*G01N 33/487* (2006.01)

(52) U.S. Cl.
CPC ..... *C12Q 1/6869* (2013.01); *G01N 27/44791* (2013.01); *G01N 33/48721* (2013.01)

(58) Field of Classification Search
CPC ............. G01N 33/48721; G01N 27/40; G01N 27/44791; C12Q 1/6869
See application file for complete search history.

(56) References Cited

U.S. PATENT DOCUMENTS

| | | |
|---|---|---|
| 7,312,155 B2 | 12/2007 | Dubin et al. |
| 7,670,770 B2 | 3/2010 | Chou et al. |
| 7,898,005 B2 | 3/2011 | Yang et al. |
| 8,097,922 B1 | 1/2012 | Balandin et al. |
| 8,105,471 B1 | 1/2012 | Han et al. |
| 8,273,532 B2 | 9/2012 | Gershow et al. |
| 8,384,195 B2 | 2/2013 | Wang et al. |
| 2001/0023986 A1 | 9/2001 | Mancevski |
| 2007/0122313 A1 | 5/2007 | Li et al. |
| 2007/0138132 A1* | 6/2007 | Barth ................. B82Y 5/00 216/56 |

(Continued)

OTHER PUBLICATIONS

S. W. Nam et al., Ionic Field Effect Transistors with Sub-10 nm Multiple Nanopores, Nano Letters, vol. 9, No. 5, pp. 2044-2048 (2009).*

(Continued)

*Primary Examiner* — Maris R Kessel
(74) *Attorney, Agent, or Firm* — Cantor Colburn LLP; Vazken Alexanian

(57) ABSTRACT

A technique is provided for controlling biomolecules in a nanodevice. A membrane has two reservoirs at opposing ends of the membrane. A nanochannel is formed in the membrane connecting the two reservoirs. A gate electrode is formed on the membrane such that the gate electrode extends laterally in a region of the nanochannel. A biomolecule is trapped in the nanochannel by applying a first voltage to the gate electrode. In response to trapping the biomolecule, the biomolecule is stretched in the nanochannel by applying a second voltage to the gate electrode. The biomolecule is stretched based on changing from the first voltage to the second voltage applied to the gate electrode.

15 Claims, 6 Drawing Sheets

(56) References Cited

U.S. PATENT DOCUMENTS

| | | | |
|---|---|---|---|
| 2008/0171316 A1* | 7/2008 | Golovchenko | C12Q 1/6869 435/6.11 |
| 2008/0242556 A1 | 10/2008 | Cao et al. | |
| 2010/0066348 A1 | 3/2010 | Merz et al. | |
| 2011/0227558 A1 | 9/2011 | Mannion et al. | |
| 2011/0279125 A1 | 11/2011 | Bedell et al. | |
| 2011/0308949 A1 | 12/2011 | Afzali-Azdakani et al. | |
| 2012/0322055 A1* | 12/2012 | Royyuru | G01N 33/48721 435/6.1 |
| 2014/0312003 A1* | 10/2014 | Peng | C12Q 1/6869 216/17 |
| 2015/0247193 A1* | 9/2015 | Holt | G01N 33/48721 506/6 |

OTHER PUBLICATIONS

B. M. Venkatesan, Highly Sensitive, Mechanically Stable Nanopore Sensors for DNA Analysis, Adv Mater., vol. 21, No. 27, pp. 2771-2776 (2009).*

E. S. Sadki, et al., Embedding a carbon nanotube across the diameter of a solid state nanopore, J. Vac. Sci. Technol. B., vol. 29, No. 5, pp. 053001-1-4 (2010).*

H. Cao, et al., "Fabrication of 10 nm Enclosed Nanofluidic Channels," Applied Physics Letters, vol. 81., No. 1., 2002, pp. 174-176.

R. Fan, et al., "DNA Translocation in Inorganic Nanotubes," Nano Letters, vol. 5., No. 9, 2005, pp. 1633-1637.

M. Gracheva, et al., "p-n Semiconductor Membrane for Electrically Tunable Ion Current Rectification and Filtering," Nano Letters, vol. 7, No. 6, 2007; pp. 1717-1722.

W. Guan, et al., "Field-Effect Reconfigurable Nanofluidic Ionic Diodes," Nature Communications, vol. 2., 2011, 506; 8 pages.

Y. He, et al., "Controlling DNA Translocation Through Gate Modulation of Nanopore Wall Surface Charges," ACS Nano, vol. 5, No. 7, 2011; pp. 5509-5518.

Y. He, et al., "Gate Manipulation of DNA Capture into Nanopores," ACE Nano, vol. 5., No. 10, 2011, pp. 8391-8397.

J. Heng, et al., "Stretching DNA Using the Electric Field in a Synthetic Nanopore," Nano Letters, vol. 5, No. 10, 2005; pp. 1883-1888.

R. Karnik, et al., "Electrostatic Control of Ions and Molecules in Nanofluidic Transistors," Nano Letters, vol. 5, No. 5., 2005; pp. 943-948.

S-W. Nam, et al., "Ionic Field Effect Transistors with sub-10 nm Multipke Nanopores," Nano Letters, vol. 9, No. 5, 2009; pp. 2044-2048.

S-W. Nam, et al., "Sub-10-nm Nanochannels by Self-Sealing and Self-Limiting Atomic Layer Deposition," Nano Letters, vol. 10, No. 9, 2010, pp. 3324-3329.

* cited by examiner

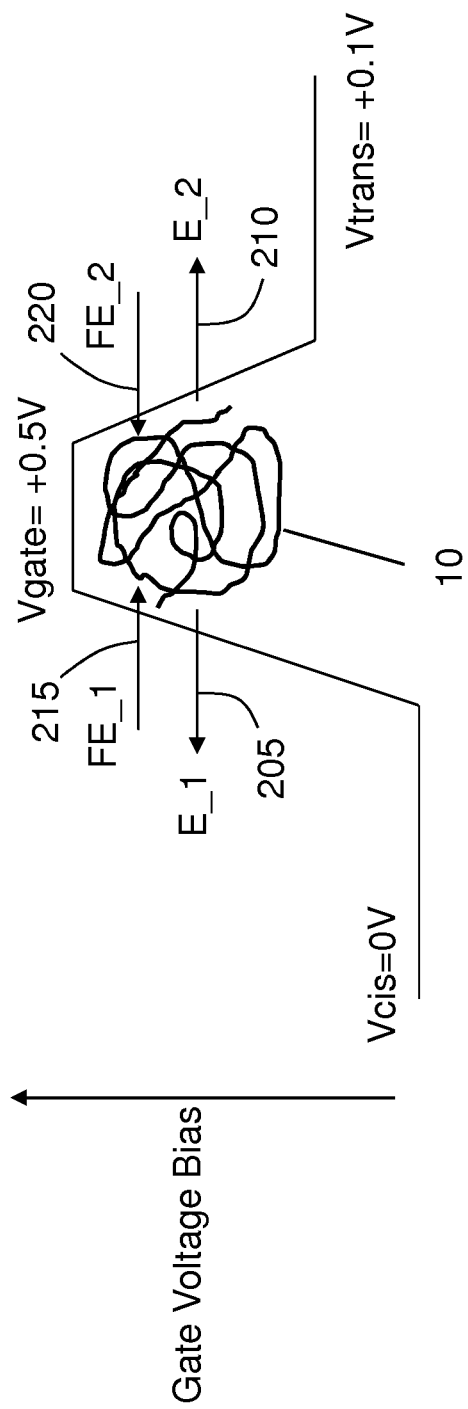
FIG. 2A Trapping: Pulling by Gate Voltage Bias

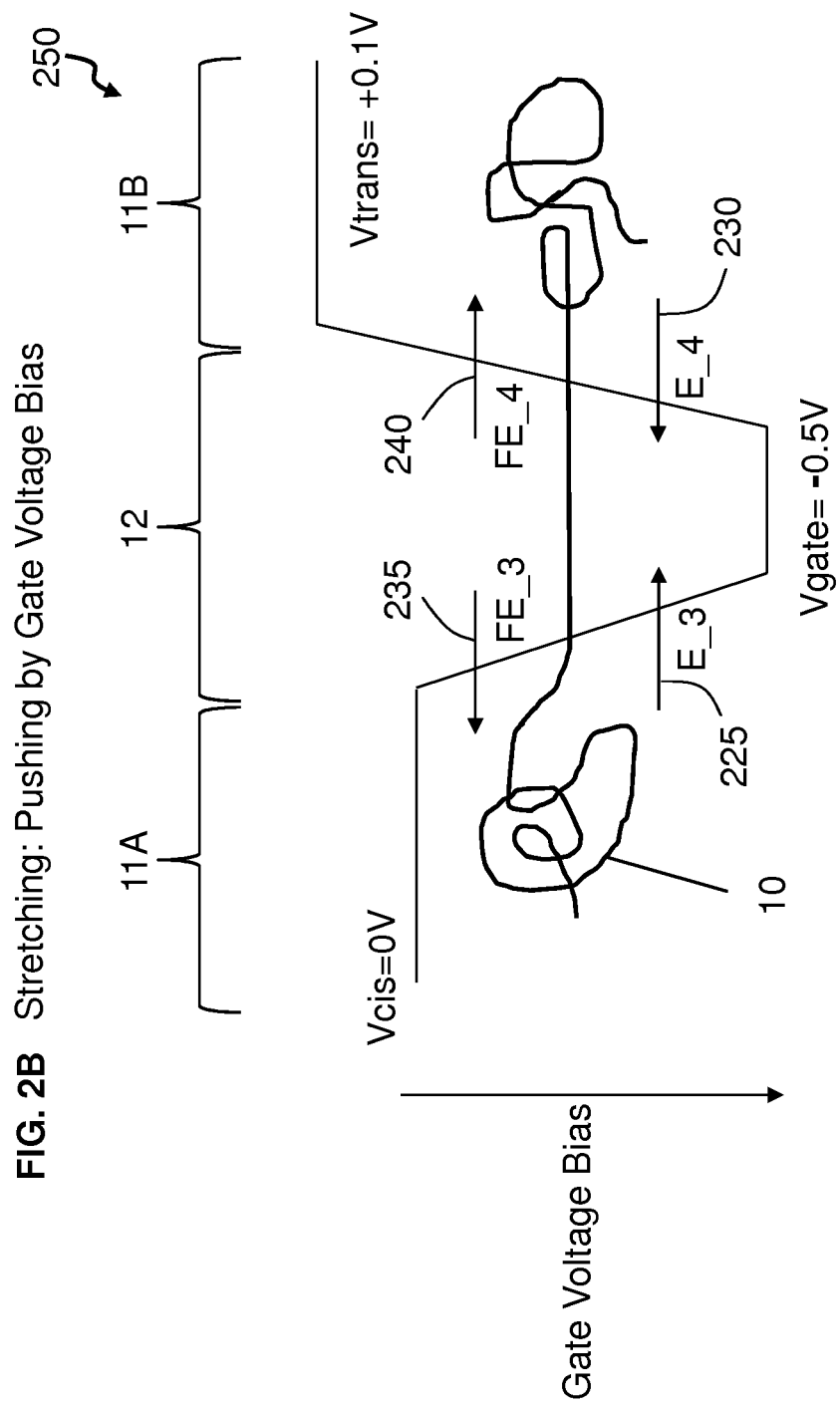
FIG. 2B  Stretching: Pushing by Gate Voltage Bias

ELECTRICAL TRAPPING AND STRETCHING OF CHARGED BIOMOLECULES BY SINGLE ELECTRODE GATING STRUCTURE

BACKGROUND

Embodiments relate to nanodevices, and more particularly to trapping and stretching charged biomolecules by a single gate electrode in a nanochannel or nanopore.

Nanopore sequencing is a method for determining the order in which nucleotides occur on a strand of deoxyribonucleic acid (DNA). A nanopore is a small hole in the order of several nanometers in internal diameter. The theory behind nanopore sequencing relates to what occurs when the nanopore is immersed in a conducting fluid (liquid electrolyte) and an electric potential difference (voltage) is applied across the nanopore. Under these conditions, a slight electric current due to conduction of ions through the nanopore can be measured, and the amount of current is very sensitive to the size and shape of the nanopore. If single-stranded DNA (ssDNA) or double-stranded DNA (dsDNA) (or single nucleotide) passes through the nanopore, this can create a change in the magnitude of the current through the nanopore. Other electrical or optical sensors can also be placed around the nanopore so that DNA bases can be differentiated while the DNA passes through the nanopore.

DNA could be driven through the nanopore by using various methods. For example, an electric field might attract the DNA towards the nanopore, and DNA might eventually pass through the nanopore.

BRIEF SUMMARY

According to an embodiment, a method for controlling biomolecules in a nanodevice is provided. The method includes providing a membrane having two reservoirs at opposing ends of the membrane. A nanochannel is formed in the membrane connecting the two reservoirs, and a gate electrode is formed on the membrane such that the gate electrode extends laterally in a region of the nanochannel. The method includes trapping a biomolecule in the nanochannel by applying a first voltage to the gate electrode, and in response to trapping the biomolecule, stretching the biomolecule in the nanochannel by applying a second voltage to the gate electrode. Stretching the biomolecule is based on changing from the first voltage to the second voltage applied to the gate electrode.

According to an embodiment, a system for controlling biomolecules in a nanochannel is provided. The nanodevice includes a membrane having two reservoirs at opposing ends of the membrane, a nanochannel formed in the membrane connecting the two reservoirs, and a gate electrode formed on the membrane such that the gate electrode extends laterally in a region of the nanochannel. A first voltage source is connected to the gate electrode, and the first voltage source applies a first voltage to the gate electrode to trap a biomolecule in the nanochannel. A second voltage source is connected to the two reservoirs via reservoir electrodes. When the second voltage source applies reservoir voltage to the two reservoirs, the first voltage source applies a second voltage to the gate electrode to stretch the biomolecule in the nanochannel. The biomolecule is stretched based on changing from the first voltage applied to the gate electrode to the second voltage.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

FIG. 2A is a voltage profile illustrating an example of trapping the biomolecule in the nanochannel using a single gate electrode according to an embodiment.

FIG. 2B is a voltage profile illustrating an example of stretching the biomolecule in the nanochannel using a single gate electrode according to an embodiment.

DETAILED DESCRIPTION

Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome. Two issues in nanopore DNA sequencing are to control the translocation (movement) of DNA through the nanopore and to differentiate DNA bases.

For the electrical trapping (controlling) of charged biomolecules in solid-state devices, a simple device structure is still needed. Until now, triple-electrodes (DNA transistor), quadruple-electrodes (Paul trap), and double-electrodes (capacitor-type structure) have been suggested as electrical-functional elements to manipulate/control charged biomolecules.

However, embodiments provide a method and device to trap and stretch charged biomolecules, such as DNA, RNA, proteins, etc., by using a single-electrode gating structure of an ion transistor.

Figure 1:
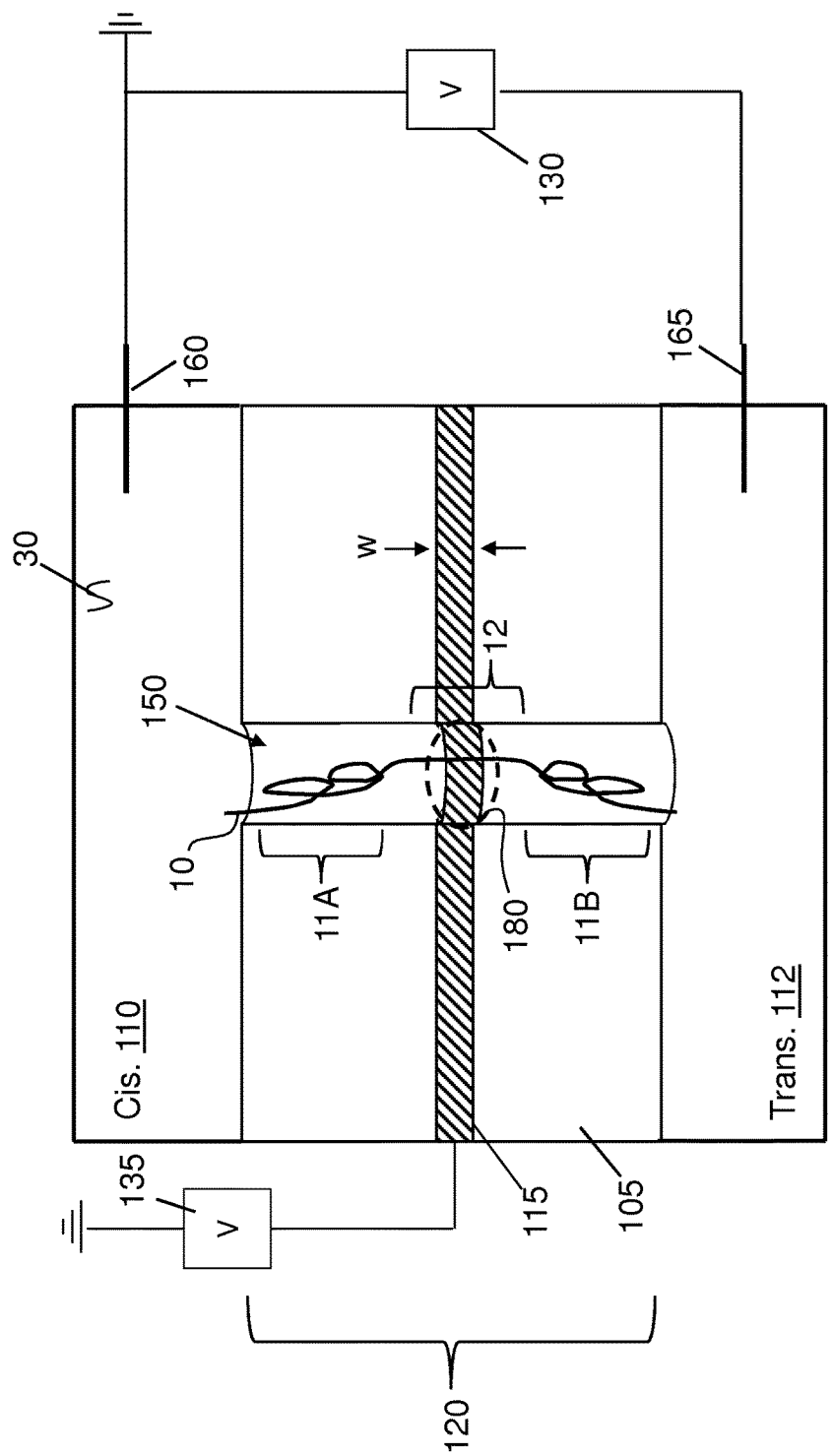
FIG. 1 is a cross-sectional view of a schematic for a nanodevice for biomolecule motion control according to an embodiment.

Now turning to FIG. 1, a cross-sectional view is illustrated of a schematic of a nanodevice 100 with a nanopore and/or nanochannel 150 for biomolecule motion control according to an embodiment. A membrane 120, which is made of a substrate 105 (an insulating layer), partitions the reservoir into two reservoir parts 110 (cis.) and 112 (trans.). The substrate 105 may be silicon oxide ($SiO_2$), silicon nitride ($Si_3N_4$) and/or any other material configured/designed not to conduct electrically.

A nanometer size nanopore/nanochannel 150 is made through the substrate 105 of the membrane 120. The substrate 105 is electrically insulating. The size of nanochannel/nanochannel 150 is the order of several nanometers. The size of nanopore/nanochannel depends on the methods of nanopore/nanochannel fabrication. TEM drilling method allows for sub-10 nm nanopore features. E-beam lithography (EBL) or focused ion beam (FIB) conventionally allows for 10 to 20 nm-level features. A single gate electrode 115 is deposited (and patterned laterally) on the substrate 105 and in the nanochannel 150. The substrate 105, the nanochannel 150, and the gate electrode 115 are all part of a membrane 120. The single gate electrode 115 is the only electrode in the membrane 120 and is the only electrode physically in and/or on the substrate 105. The substrate 105 may be an insulating layer with the gate electrode 115 laterally deposited across the insulating layer, so as to be deposited in the nanochannel 150. The nanopore/nanochannel 150 may be formed by transmission electron microscopy (TEM), focused ion beam (gallium ion (Ga+) beam), helium ion microscopy, dry etching (including reactive ion etching), wet etching, isotropic gas-phase etching, and other techniques known in the art.

One end of the membrane 120 is sealed to the (cis.) reservoir 110 (e.g., top reservoir) and the opposite end of the membrane 120 is sealed to the (trans.) reservoir 112 (e.g., bottom reservoir). An electrolyte solution 30 fills the reservoirs 110 and 112 and the nanochannel 150. The electrolyte solution 30 is a conductive fluid, such as a salt solution with ions for conducting electricity when voltage is applied.

Biomolecules 10 may be added to the top chamber/reservoir 110 and then captured at the entrance of the nanochannel 150. Two electrochemical electrodes 160 and 165 are respectively dipped in reservoirs 110 and 112 and operatively connected to a voltage source 130. The biomolecule 10 (such as DNA, RNA, protein) is loaded/captured into the nanopore/nanochannel 150 by an electrical voltage bias of the voltage source 130 applied across the nanochannel 150 via the two electrochemical electrodes 160 and 165. In a conventional system, the biomolecule would simply pass through the nanochannel 150.

According to embodiments, a method is utilized to trap and stretch the charged biomolecule 10 (which may be, e.g., a single-stranded (ssDNA) molecule), by using an ion transistor device (i.e., the nanodevice 100). Ion transistor refers to a nanopore/nanochannel fluidic device (i.e., nanodevice 100) having three-terminals such as a source terminal (e.g., electrode 160), drain terminal (e.g., electrode 165), and gate terminal (e.g., gate electrode 115). The separate source and drain reservoirs 110 and 112 are connected by the nanopore/nanochannel 150 which is coupled with metal gate electrode 115. The single gate electrode structure (i.e., membrane 120) electrically controls (by the polarity of the gate electrode 115) the transport of biomolecules 10 through nanopore/nanochannel 150. The gate voltage (i.e., gate voltage bias) is applied by a voltage source 135 connected to the gate electrode 115.

The gate electrode 115 may be made of metal, such as gold (Au), silver (Ag), aluminum (Al), ruthenium (Ru), copper (Cu), cobalt (Co), nickel (Ni), palladium (Pd), platinum (Pt), titanium (Ti), tantalum (Ta), titanium nitride (TiN), tantalum nitride (TaN) and/or other alloys. In addition, the gate electrode 115 can be transparent conducting oxide (TCO) materials such as indium-tin-oxide (ITO), zinc oxide (ZnO) and/or other alloys. The gate electrode 115 can be conducting semiconductor materials such as doped silicon (Si), germanium (Ge), gallium arsenide (GaAs), gallium nitride (GaN) and/or other alloys. The gate electrode 115 can be carbon-based nanostructures such as carbon nanotube (CNT), graphene and graphite. In one embodiment, the gate electrode 115 may be a metal strip with a width (w) of about 10 nm to 2 micrometers ($\mu m$). In another embodiment, the width (w) of the gate electrode 115 may be sub 10 nm.

Note that gate electrodes generally have a ring-shape, surrounding-shape, or planar-shape structure. The gate electrode 115 is perpendicular to the length of the nanochannel 150. By controlling the polarity of the gate voltage (applied by the voltage source 135), the single electrode gating operation enables trapping and stretching of ssDNA and any other type of biomolecule 10. In one embodiment, the voltage sources 130 and 135 may be implemented (and controlled) in a computer test setup discussed further in FIG. 5 below.

An example of trapping and stretching the biomolecule 10 is provided below. It is assumed that the biomolecule 10 (e.g., ssDNA) is a negatively charged biomolecule in this example, and it is understood that positively charged biomolecules apply by analogy.

The voltage of voltage source 130 generates an electric field between the electrodes 160 and 165, and the force of the electric field drives the biomolecule 10 into the nanochannel 150. While the biomolecule 10 (e.g., assuming a negatively charged biomolecule 10) is in the nanochannel 150 (and the biomolecule 10 extends/crosses over the gate electrode 115), a gate voltage bias with a positive polarity (for instance+0.5 volts (V)) is applied to the gate electrode 115 by the voltage source 135. The positive polarity of the gate voltage (on the gate electrode 115) generates an electrical potential trap, thus leading coiled ssDNA molecules (persistence length <~2 nm) to be captured and immobilized near the wall of gate electrode 115 and dielectric material of the substrate 105. In other words, the biomolecule 10 is pulled down to the gate electrode 115 (and pulled down to the area/region 180 of the substrate 105 near the gate electrode 115). After having trapped the biomolecule 10 in place such that the biomolecule 10 cannot move further through (or backwards) the nanochannel 150, the polarity of the gate voltage (applied by the voltage source 135) is reversed to a negative gate voltage on the gate electrode 115. The negative polarity of the gate voltage bias (for instance −0.5 V) induces opposite directions of electric field both pointing toward each other in the nanochannel, which create forces (pointing away from one another) that drive the coiled ssDNA biomolecule 10 to move in two opposite directions. Therefore, the ssDNA biomolecule 10 is stretched by a shaping dumbbell-geometry, in which two separately-coiled ssDNA fragments 11A and 11B are connected by a stretched part 12 passing through the middle of the gate electrode 115 coupled nanochannel 150 region 180 as shown in FIG. 2B. The method is particularly beneficial in a nanochannel structure, where the stretching of ssDNA is not achieved unless the nanochannel dimension is decreased less than the persistence length of ssDNA.

According to an embodiment, FIG. 2A is a voltage profile 200 illustrating an example of trapping the biomolecule 10 (e.g., DNA) in the nanochannel 150 of the nanodevice 100 using the single gate electrode 115 in the membrane 120. FIG. 2B is a voltage profile 250 illustrating stretching the biomolecule 10 in the nanochannel 150 of the nanodevice 100 using the single gate electrode 115 in the membrane 120 according to an embodiment. FIGS. 2A and 2B may generally be referred to as FIG. 2. Note that the details of the nanodevice 100 (shown in FIG. 1) are omitted so as not to obscure FIG. 2, but it is contemplated that the elements in FIG. 1 are meant to be included.

First, details of the trapping behavior are shown in FIG. 2A. A voltage is applied between electrodes 160 and 165 by voltage source 130, in order to drive the negatively charged biomolecule 10 into the nanochannel 150. Once in the nanochannel 150, a +0.5 V gate voltage (positive polarity) of the gate electrode 115 is turned on by voltage source 135. The positive polarity of the gate voltage traps the negatively charged biomolecule 10 in the nanochannel 150, by drawing/pulling the biomolecule 10 down to the gate electrode 115 and the substrate 105 (this may be referred to as the gate electrode region 180 within the nanochannel 150). As a result of the +0.5 V gate voltage, two electric fields 205 (E_1) and 210 (E_2) in the nanochannel 150 create a trapping potential well for the negatively charged biomolecule 10. The electric fields 205 and 210 create forces 215 (FE_1) and 220 (FE_2) that hold the negatively charged biomolecule 10 in place within the nanochannel 150.

Second, once trapped in place, details of the stretching are further shown in FIG. 2B. As applied by the voltage source 130, assume that the voltage ($V_{Cis}$) on electrode 160 is 0 volts (in the top/cis reservoir 110) and the voltage ($V_{Trans}$) on electrode 165 is 0.1 volts (in the bottom/trans reservoir 112). Also, assume now that −0.5 volts is applied to the gate electrode 115 at this time. Accordingly, the gate voltage (−0.5 V) is less than the voltage on the electrode 160 (0 V) in the top reservoir 110 and less than the voltage on the electrode 165 (0.1 V) in the bottom reservoir 112. The negative voltage on the gate electrode 115 creates two electric fields 225 (E_3) and 230 (E_4) in the nanochannel 150. The electric field 225 (E_3) points from the 0 V on the electrode 160 in the top reservoir 110 to the −0.5 V gate voltage of the gate electrode 115. The electric field 230 (E_4) points from the 0.1 V on the electrode 165 in the bottom reservoir 112 to the −0.5 V gate voltage of the gate electrode.

The electric field 225 creates a force 235 (FE_3) that pushes the biomolecule 10 to the left, whereas the electric field 230 (E_4) creates a force 240 (FE_4) that pushes the biomolecule 10 to the right. The repulsing forces 235 and 240 stretch the biomolecule 10, as shown in FIG. 2B. Viewed from left to right, the negatively charged biomolecule 10 has coiled part 11A, followed by stretched/straightened part 12, and then followed by coiled part 11B, all of which is a result of the forces 235 and 240.

Figure 3:
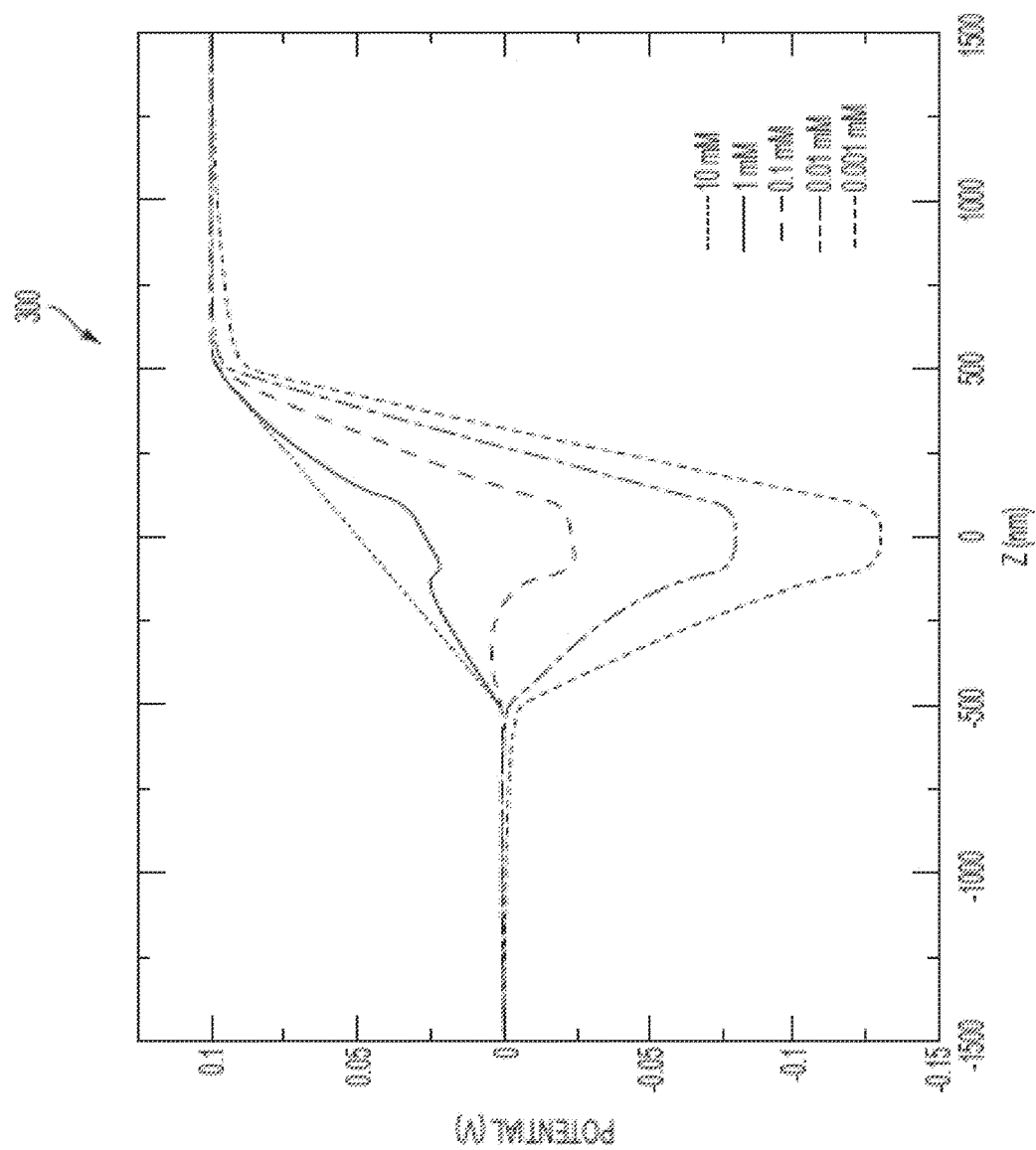
FIG. 3 is a graph illustrating a potential (voltage) profile in the nanochannel for different ion concentrations of electrolyte solutions according to an embodiment.

Now turning to FIG. 3, a graph 300 is illustrated of a potential (voltage) profile from cis. to trans. reservoirs (chambers) 110 and 112 according to an embodiment. The y-axis shows the voltage on the gate electrode 115 inside the nanochannel 150, and the x-axis shows vertical position (z) of movement of the biomolecule for different ion concentrations in the electrolyte solution 30.

In this example, the gate voltage (on the gate electrode 115) is −0.2 V (at which trapping occurs). The applied source and drain voltages respectively on the electrodes 160 and 165 are 0 and 0.1 V. Ion concentrations in the electrolyte solution 30 vary from about 0.001 to about 10 mM (millimole).

When the gate voltage bias (e.g., −0.2V) is applied on the gate electrode 115, a trapping potential is created inside the nanochannel 150 in graph 300 for the ion concentration of 0.001 mM. When ion concentration is low, such as 0.1 mM, potentials around the gate electrode 115 are reduced, which can be used to trap positively charged molecule. Accordingly, when applying a positive gate voltage on the gate electrode 115, negatively charged molecules (such as DNA) can be trapped at (the region 180 of) the gate electrode 115 in the nanochannel 150. In a high ion-concentration electrolyte solution 30 (such as 100 mM), because of the ion-screening effect, the potential profile through the nanochannel 150 is not affected by the gate electrode 115.

For a lower ion-concentration electrolyte solution 30, the gate voltage on the gate electrode 115 (to trap the biomolecule 10) can be lower.

Figure 4:
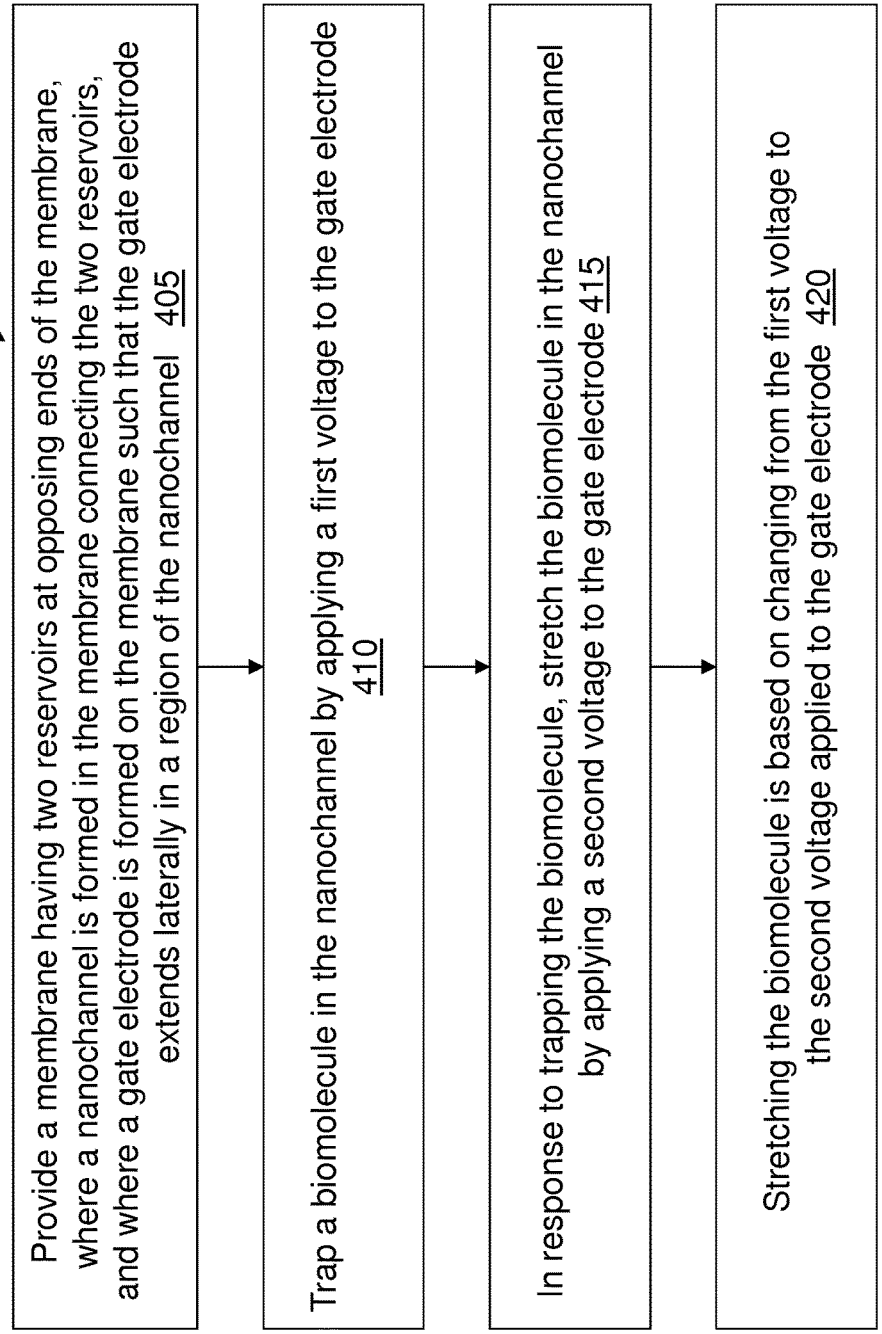
FIG. 4 is a flow chart of a method for controlling biomolecules in the nanodevice according to an embodiment.

FIG. 4 illustrates a method 400 for controlling (trapping and stretching) biomolecules 10 in the nanodevice 100. Reference can be made to FIGS. 1-3, along with FIG. 5 (discussed below).

At block 405, the membrane 120 is provided which has two reservoirs 110 and 112 sealably attached at opposing ends of the membrane 120, where the nanochannel 150 is formed in the membrane 120 connecting the two reservoirs 110 and 112, and where the gate electrode 115 is formed on the membrane 120 such that the gate electrode 115 extends laterally in the region 180 of the nanochannel 150. The two reservoirs 110 and the nanochannel 150 are filled with the electrolyte solution 30.

At block 410, the voltage source 135 applies a first voltage to the gate electrode 115 in order to trap the biomolecule 10 in the nanochannel 150.

At block 415, in response to trapping the biomolecule 10 in the nanochannel 150, the voltage source 135 applies a second voltage to the gate electrode 115 in order to stretch the biomolecule 10 in the nanochannel 150.

At block 420, the stretching of the biomolecule 10 is based on changing (polarity) from the first voltage (for trapping) to the second voltage (for stretching) applied to the gate electrode 115.

The first voltage is a different polarity from the second voltage. In one embodiment, the first voltage (for trapping) applied to the gate electrode 115 may be +0.5 V (when the biomolecule is negatively charged) and the second voltage (for stretching) applied to the gate electrode 115 may be −0.5 V.

The biomolecule has a charge, such that the biomolecule 10 is either negatively charged or positively charged. The first voltage is applied with a first polarity that is opposite the charge on the biomolecule. For example, when the biomolecule 10 is positively charged, the first voltage has a negative polarity (e.g., −0.5). When the biomolecule 10 is negatively charged, the first voltage has a positive polarity (e.g., +0.5). Applying the first voltage with the first polarity opposite the charge on the biomolecule 10 pulls the biomolecule down to the region 180 of the gate electrode 115 in the nanochannel 150.

The second voltage is applied (by the voltage source 135) with a second polarity that is the same as the charge on the biomolecule. For example, when the biomolecule 10 is negatively charged the second voltage is a positive polarity (e.g., +0.5). When the biomolecule 10 is positively charged, the second voltage has a negative polarity (e.g., −0.5). Applying the second voltage with the second polarity the same as the charge on the biomolecule 10 pulls (pushes) the first coiled part 11A of the biomolecule 10 in one direction and pulls (pushes) the second coiled part 11B in an opposite direction, such that pulling (pushing) the biomolecule 10 in two opposite directions causes a straightened part 12 between the first and second coiled parts 11A and 11B of the biomolecule 10.

The membrane 120 only has one electrode formed therein and the one electrode is the gate electrode 115. The gate electrode 115 is formed in or deposited on the substrate 105.

With regard to the membrane 120, no other electrodes (physically) touch membrane 120 except the gate electrode 115, no other electrodes are electrically connected to the membrane 120 except the gate electrode 115, no other electrodes are in the nanochannel 150 except the gate electrode 115, and/or no electrodes on the membrane 120 and in the nanochannel 150 cause trapping and stretching except the gate electrode 115.

The reservoir voltage is applied (by voltage source 130) between cis and trans reservoirs (i.e., electrodes 160 and 165). The second voltage (e.g., −0.5 V) applied on the gate electrode 115 together with the cis-reservoir voltage (e.g., 0 V) causes a pulling/pushing force 235 (FE_3) on the biomolecule 10 toward the first (cis) reservoir 110. The second voltage (e.g., −0.5 V) applied on the gate electrode 115 together with the trans-reservoir voltage (+0.1 V) causes a pulling/pushing force 240 (FE_4) on the biomolecule 10 toward the second (trans) reservoir 112. For stretching, the voltage/potential of the cis and trans reservoir voltages is higher than the second voltage on the gate electrode.

The second gate voltage applied on the gate electrode 115 has an opposite polarity to the first gate voltage.

The biomolecule 10 may be a DNA molecule, an RNA molecule, and/or a protein.

Figure 5:
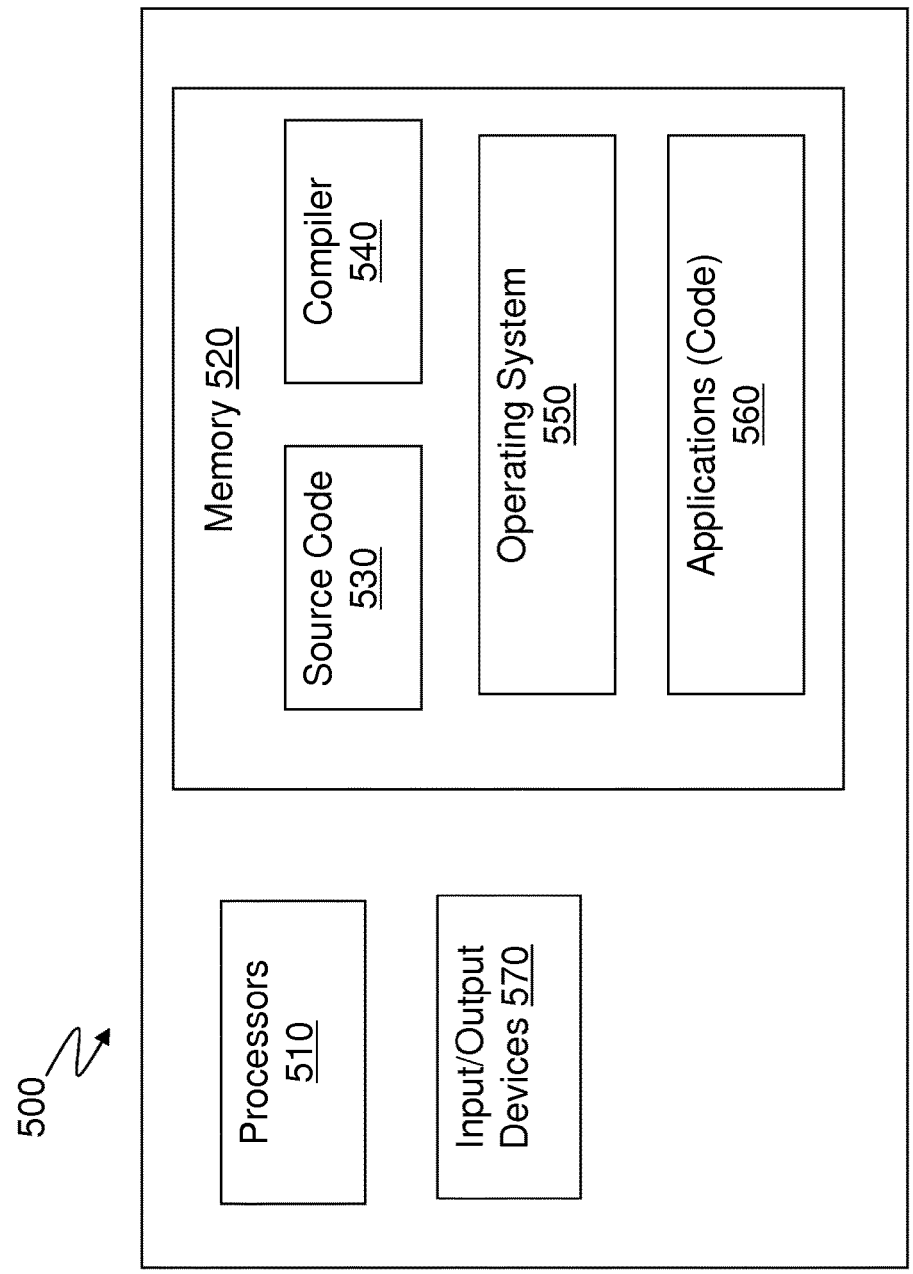
FIG. 5 illustrates a computer test setup which may implement, control, and/or regulate features discussed herein according to an embodiment.

FIG. 5 illustrates an example of a computer 500 (e.g., as part of the computer test setup for testing and analysis) which may implement, control, and/or regulate the respective voltages of the voltage sources, respective measurements of ammeters, and display screens for displaying various current amplitude as would be understood to one skilled in the art.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art. For example, the computer 500 which may be any type of computing device and/or test equipment (including ammeters, voltage sources, current meters, connectors, etc.). Input/output device 570 (having proper software and hardware) of computer 500 may include and/or be coupled to the nanodevices and structures discussed herein via cables, plugs, wires, electrodes, patch clamps, pads, etc. Also, the communication interface of the input/output devices 570 comprises hardware and software for communicating with, operatively connecting to, reading, and/or controlling voltage sources, ammeters, and current traces (e.g., magnitude and time duration of current), etc., as understood by one skilled in the art. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, Labview software or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method for controlling biomolecules in a nanodevice, the method comprising:
   providing a membrane having two reservoirs at opposing ends of the membrane, wherein a nanochannel is formed in the membrane connecting the two reservoirs such that the nanochannel is formed of a membrane curved part of the membrane, wherein a single gate electrode is formed on the membrane such that the single gate electrode extends laterally in a region of the nanochannel, the membrane being void of any other electrode formed on the membrane, wherein the single gate electrode is formed at a longitudinal position on the membrane such that a portion of the membrane is both above and below in a length direction of the nanochannel, wherein the length direction of the nanochannel connects the two reservoirs, wherein the single gate electrode comprises a curved part physically contacting the membrane curved part of the nanochannel and the single gate electrode comprises a straight part outside of the nanochannel such that the curved and straight parts of the single gate electrode physically contact one another at an edge of the membrane curved part, the straight part extending to an end of the membrane;
   trapping a biomolecule in the nanochannel by applying a gate voltage to the single gate electrode; and
   in response to trapping the biomolecule, stretching the biomolecule in the nanochannel by applying the gate voltage to the single gate electrode, wherein stretching the biomolecule is based on changing from a first value to second value for the gate voltage applied to the gate electrode;
   wherein stretching the biomolecule simultaneously comprises:
      applying a first voltage to a first electrode in a first reservoir of the two reservoirs and to a second electrode in a second reservoir;
      causing a pushing force on the biomolecule toward the second reservoir by applying the gate voltage on the single gate electrode together with the first voltage while the membrane is void of any other electrode formed on the membrane;
      causing a pushing force on the biomolecule toward the first reservoir by applying the gate voltage on the single gate electrode together with the first voltage while the membrane is void of any other electrode formed on the membrane; and
      applying the gate voltage on the gate electrode with the second value being less than a value of the first voltage, while the value for the first voltage is higher on the second electrode in the second reservoir than the first electrode in the first reservoir;
      wherein the single gate electrode has been patterned in the nanochannel itself.

2. The method of claim 1,
   wherein the longitudinal position is about centrally located along the length of the nanochannel.

3. The method of claim 1, wherein the biomolecule has a charge, such that the biomolecule is either negatively charged or positively charged.

4. The method of claim 3, further comprising applying the first voltage with a first polarity that is opposite the charge on the biomolecule.

5. The method of claim 4, wherein applying the first voltage with the first polarity opposite the charge on the biomolecule pulls the biomolecule down to the region of the gate electrode in the nanochannel.

6. The method of claim 1, wherein the biomolecule is at least one of a DNA molecule, an RNA molecule, or a protein.

7. The method of claim 1, wherein the single gate electrode is selected from the group consisting of gold, silver, ruthenium, copper, cobalt, nickel, palladium, platinum, tantalum, and tantalum nitride.

8. The method of claim 1, wherein the single gate electrode is a transparent conducting oxide.

9. The method of claim 1, wherein the single gate electrode is a carbon-based nanostructures.

10. The method of claim 1, wherein the single gate electrode is a conducting semiconducting material that has been doped.

11. The method of claim 1, wherein the single gate electrode is both in the nanochannel itself and extends outside the nanochannel, such that the single gate electrode extends continuously an entire width of the membrane.

12. The method of claim 1, wherein the portion of the membrane is a dielectric material both above and below the single gate electrode;
   wherein the dielectric material is sandwiched directly between the first reservoir and the single gate electrode in one direction;

wherein the dielectric material is sandwiched directly between the second reservoir and the single gate electrode in another direction.

13. The method of claim 1, wherein the dielectric material of the membrane is directly adjacent to the first reservoir and the second reservoir.

14. The method of claim 1, wherein the single gate electrode comprises another straight part outside of the nanochannel such that the curved and another straight parts of the single gate electrode physically contact one another at an opposite edge of the membrane curved part, the another straight part extending to an opposite end of the membrane.

15. The method of claim 1, wherein the end of the membrane is a termination for both the membrane and the straight part extending.

* * * * *